United States Patent [19]

Theissen

[11] Patent Number: 4,681,622

[45] Date of Patent: * Jul. 21, 1987

[54] SUBSTITUTED PHENOXYBENZOIC ACIDS AND DERIVATIVES THEREOF AS HERBICIDES

[75] Inventor: Robert J. Theissen, Bridgewater, N.J.

[73] Assignee: Rhone-Poulenc Agrochimie, Lyons, France

[*] Notice: The portion of the term of this patent subsequent to Aug. 14, 1996 has been disclaimed.

[21] Appl. No.: 587,973

[22] Filed: Mar. 9, 1984

Related U.S. Application Data

[63] Continuation of Ser. No. 490,357, May 2, 1983, abandoned, which is a continuation of Ser. No. 181,491, Sep. 4, 1980, abandoned, which is a continuation of Ser. No. 837,957, Sep. 29, 1977, abandoned, which is a continuation of Ser. No. 702,367, Jul. 2, 1976, Pat. No. 4,606,758, which is a continuation-in-part of Ser. No. 617,569, Sep. 29, 1975, Pat. No. 3,979,437, which is a continuation of Ser. No. 398,610, Sep. 19, 1973, Pat. No. 3,941,830, which is a continuation of Ser. No. 114,712, Feb. 11, 1971, Pat. No. 3,784,635, which is a continuation-in-part of Ser. No. 819,412, Apr. 25, 1969, Pat. No. 3,652,645, said Ser. No. 702,367, is a continuation-in-part of Ser. No. 545,232, Jan. 29, 1975, Pat. No. 4,002,662, which is a continuation-in-part of Ser. No. 398,610, Sep. 19, 1973, Pat. No. 3,941,830.

[51] Int. Cl.$^4$ ............................................. A01N 33/22
[52] U.S. Cl. ........................................ 71/108; 71/98; 71/105; 71/115; 71/116
[58] Field of Search .................. 71/98, 103, 105, 115, 71/116, 108, 118; 260/465 D, 544 N; 562/435; 560/21

[56] References Cited

U.S. PATENT DOCUMENTS

| | | | |
|---|---|---|---|
| Re. 30,361 | 8/1980 | Bayer et al. | 260/465 F |
| 3,316,080 | 4/1967 | Inoue et al. | 71/124 |
| 3,322,525 | 5/1967 | Martin et al. | 71/103 X |
| 3,423,470 | 1/1969 | Rohr et al. | 71/105 |
| 3,652,645 | 3/1972 | Theissen | 71/115 X |
| 3,755,449 | 8/1973 | Ito et al. | 260/571 |
| 3,776,715 | 12/1973 | Theissen | 71/115 X |
| 3,784,635 | 1/1974 | Theissen | 71/115 X |
| 3,798,276 | 3/1974 | Bayer et al. | 71/98 X |
| 3,812,184 | 5/1974 | Theissen | 71/115 X |
| 3,839,444 | 10/1974 | Theissen | 564/116 |
| 3,873,302 | 3/1975 | Theissen | 71/115 X |
| 3,873,303 | 3/1975 | Theissen | 71/118 |
| 3,907,866 | 9/1975 | Theissen | 71/111 X |
| 3,928,416 | 12/1975 | Bayer et al. | 71/105 |
| 3,929,455 | 12/1975 | Theissen | 71/92 X |
| 3,941,830 | 3/1976 | Theissen | 560/21 |
| 3,953,489 | 4/1976 | Tamura et al. | 260/455 R |
| 3,979,437 | 9/1976 | Theissen | 71/111 X |
| 3,983,168 | 9/1976 | Theissen | 71/108 X |
| 4,001,005 | 1/1977 | Theissen | 71/108 |
| 4,002,662 | 1/1977 | Theissen | 71/105 X |
| 4,015,975 | 4/1977 | Tamura et al. | 71/100 |
| 4,039,588 | 8/1977 | Wilson et al. | 71/124 X |
| 4,063,929 | 12/1977 | Bayer et al. | 71/115 |
| 4,076,741 | 2/1978 | Bayer et al. | 71/105 X |
| 4,164,408 | 8/1979 | Theissen | 71/105 X |
| 4,164,409 | 8/1979 | Theissen | 71/105 X |
| 4,164,410 | 8/1979 | Theissen | 71/105 X |
| 4,339,268 | 7/1982 | Theissen | 71/108 |
| 4,340,417 | 7/1982 | Theissen | 71/91 |

FOREIGN PATENT DOCUMENTS

| | | |
|---|---|---|
| 634170 | 1/1962 | Canada . |
| 951651 | 3/1964 | United Kingdom . |
| 1251389 | 10/1971 | United Kingdom . |

OTHER PUBLICATIONS

Scarborough et al, J. Chem. Soc., London (1934), pp. 52–56.
Sus et al, Annalem Der Chemie, vol. 593 (1955), pp. 91–126.
Cook et al, J. Am. Chem. Soc. (1902), vol. 24, pp. 1200–1204.
Cook et al, American Chemical Journal (1902), vol. 28, pp. 486–490.
Mayer et al, Ber. (1922), pp. 1659–1666.
Borsche, Ber. (1923), pp. 1488–1493.
McCombie et al, J. Chem. Soc., London (1931), pp. 529–536.
Brewster et al, J. Am. Chem. Soc. (1934) (56), pp. 117–120.
Tozer et al, J. Chem. Soc., London (1938), pp. 1897–1900.
Koelsch et al, J. Am. Chem. Soc. (1949), vol. 71, pp. 3556–3558.
Barry et al, Proceedings of the Royal Irish Academy, Dublin (1949), pp. 55–59.
Vanderhaeghe et al, Bull. Soc. Chim., Belg. (1952), vol. 61, pp. 310–321.
Mann et al, J. Chem. Soc., London (1951), pp. 747–756.
Julia, Bull. Soc. Chim., Fr., (1952), pp. 546–549.
Julia, C. R., 1st Semestre, Academie des Sciences, Paris (1952), vol. 234, pp. 1179–1181.
Goldberg et al, J. Chem. Soc., London (1953), pp. 1348–1357 and 2049–2052.
Thompson et al, Antibiotics and Chemotherapy, N.Y. (1953), vol. 3, pp. 399–408.
Southwick et al, J. Am. Chem. Soc. (1953), pp. 5877–5880.
Tomita et al, J. Pharm. Soc., Japan (1955), vol. 75, pp. 449–461.
Fults et al, J. Amer. Soc. Agronomy, vol. 31, (1947), pp. 667–681.

Primary Examiner—Joseph Paul Brust
Attorney, Agent, or Firm—Morgan & Finnegan

[57] ABSTRACT

2-Nitro-5-(substituted-phenoxy) benzoic acids and esters, salts, amides, and acyl halides thereof comprise a class of compounds that are highly effective herbicides.

15 Claims, No Drawings

SUBSTITUTED PHENOXYBENZOIC ACIDS AND DERIVATIVES THEREOF AS HERBICIDES

CROSS-REFERENCE TO RELATED APPLICATIONS

This application is a continuation of application Ser. No. 490,357 filed May 2, 1983, now abandoned, which is a continuation of application Ser. No. 181,491 filed Sept. 4, 1980, now abandoned, which is a continuation of copending application Ser. No. 837,957 filed Sept. 29, 1977, now abandoned, which is a continuation of Ser. No. 702,367, filed July 2, 1976, now U.S. Pat. No. 4,606,758, which is a continuation-in-part of copending application Ser. No. 617,569, filed Sept. 29, 1975, now U.S. Pat. No. 3,979,437 which is a continuation of copending application Ser. No. 398,610, filed Sept. 19, 1973, now U.S. Pat. No. 3,941,830, which is a continuation of application Ser. No. 114,712, filed Feb. 11, 1971, now U.S. Pat. No. 3,784,635, which is a continuation-in-part of application Ser. No. 819,412, filed Apr. 25, 1969, now U.S. Pat. No. 3,652,645, said Ser. No. 702,367, (now U.S. Pat. No. 4,606,758) is a continuation-in-part of Ser. No. 545,232, Jan. 29, 1975, U.S. Pat. No. 4,002,662, which is a continuation-in-part of Ser. No. 398,610, Sept. 19, 1973, U.S. Pat. No. 3,941,830.

BACKGROUND OF THE INVENTION

1. Field of the Invention

This invention is concerned with certain phenoxybenzoic acid compounds and their use as herbicides.

2. Description of the Prior Art

It has been proposed to use as herbicides 2-methoxybenzoic acids (U.S. Pat. No. 3,013,054) and 4-phenoxybenzoic acids (France No. 1,502,538). It is the discovery of this invention, however, that benzoic acids having a phenoxy substituent in the 5-position are very effective herbicides.

SUMMARY OF THE INVENTION

This invention provides herbicidal compounds having the formula:

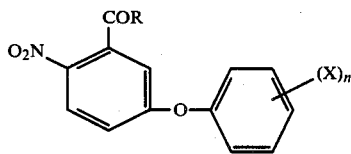

wherein X is a member selected from the group consisting of hydrogen, halogen (e.g., iodine, fluorine, chlorine and bromine), nitro trifluoromethyl, cyano, COOH,

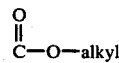

(e.g. alkyl of 1 to 4 carbon atoms), hydroxy, alkoxy of 1 to 4 carbon atoms, alkyl of 1 to 4 carbon atoms,

$SH$, $SR_1$, $SOR_1$, $SO_2R_1$, $SO_2NH_2$ and combination thereof, $R_1$ and $R_2$ are selected from the group consisting of alkyl of 1 to 4 carbon atoms, R is selected from the group consisting of hydroxy, alkoxy of 1 to 5 carbon atoms, aryloxy, chloro, amido, alkylamido of 1 to 4 carbon atoms, dialkylamido of 2 to 6 carbon atoms, SH, $SR_1$, and OM in which M is an alkali metal (e.g., lithium sodium and potassium), alkylammonium of 1 to 4 carbon atoms or alkanolammonium of 1 to 4 carbon atoms, n is an integer of 1 to 5, and in which compound at least one X is other than hydrogen; their use as herbicides; and a herbicidal composition comprising at least one of said compounds and a carrier therefor.

DESCRIPTION OF SPECIFIC EMBODIMENTS

The compounds of this invention are readily prepared by the Ullmann ether synthesis reaction between the alkali metal, (e.g., Na, K) salt of a suitable substituted phenol and a 5-halo (e.g., F, Cl, Br)-2-nitrobenzoic acid or an ester, amide, or salt thereof. The 5-halo-2-nitro-benzoic acid or ester is readily prepared by nitrating a m-halotoluene, followed by oxidation of the methyl group by well-known procedures. Also, the m-halobenzoic acid or ester may be directly nitrated by well-known procedures.

Non-limiting examples of the compounds of this invention are:
propyl 2-nitro-5-(2',4',6'-tribromophenoxy)benzoate;
phenyl 2-nitro-5-(2',4',5'-trifluorophenoxy)benzoate;
2-nitro-5-(2',4',6'-triiodophenoxy)benzoic acid;
2-nitro-5-(2',4',6'-trichlorophenoxy)benzoyl chloride;
2-nitro-5-(2',4',6'-trichlorophenoxy)benzamide;
N-ethyl 2-nitro-5-(2',4',6'-trichlorophenoxy)benzamide;
N-isopropyl 2-nitro-5-(2',4',6'-trichlorophenoxy)benzamide;
N,N-dimethyl 2-nitro-5-(2',4',6'-trichlorophenoxy)benzamide;
ethylammonium 2-nitro-5-(2',4',6'-trichlorophenoxy)benzoate;
ethanolammonium 2-nitro-5l-(2',4',6'-trichlorophenoxy)benzoate;
methyl 2-nitro-5-(2',3',4',5',6'-pentachlorophenoxy)benzoate;
n-pentyl 2-nitro-5-(2',4',6'-trichlorophenoxy)benzoate;
2-nitro-5-(2',4'-dichlorophenoxy)benzoic acid;
methyl 2-nitro-5-(2'-chlorophenoxy)benzoate;
methyl 2-nitro-5-(4'-chloro-3'-methylphenoxy)benzoate;
methyl 2-nitro-5-(3'-methylphenoxy)benzoate;
ethyl 2-nitro-5-(2',6'-dichlorophenoxy)benzoate;
isopropyl 2-nitro-5-(2',4'-dichloro-6'-methylphenoxy)benzoate;
ethyl 2-nitro-5-(2'-chloro-4'-fluorophenoxy)benzoate;
2-nitro-5-(2'-chloro-4'-fluorophenoxy)benzoic acid;
methyl 2-nitro-5-(2',4'-dinitrophenoxy)benzoate;
2-nitro-5-(2',4'-dinitrophenoxy)benzoic acid;
2-nitro-5-(2'-chloro-4'-nitrophenoxy)benzoic acid;
isopropyl 2-nitro-5-[3'-(α,α,α-trifluoromethyl)phenoxy]benzoate;
isopropyl 2-nitro-5-[3',5'-dicarbomethoxyphenoxy]benzoate;
methyl 2-nitro-5-(2'-methoxyphenoxy)benzoate;
methyl 2-nitro-5-(4'-chloro-2'-nitrophenoxy)benzoate;
2-nitro-5-(2',4'-dichloro-6'-fluorophenoxy)benzoic acid;
methyl 2-nitro-5-(2',4'-dichloro-6'-fluorophenoxy)benzoate;
methyl 2-nitro-5-(2',4'-dicarbomethoxyphenoxy)benzoate;

methyl 2-nitro-5-[2'-cyano-4'-(α,α,α-trifluoromethyl)-phenoxy]benzoate;

methyl 2-nitro-5-(3'-carbomethoxy-4'-hydroxyphenoxy)benzoate;

methyl 2-nitro-5-[4'-chloro-2'-(α,α,α-trifluoromethyl)-phenoxy]benzoate;

methyl 2-nitro-5-(3'-carbomethoxy-4'-nitrophenoxy)-benzoate;

methyl 2-nitro-5-(4'-chloro-2',6'-dibromophenoxy)benzoate;

methyl 2-nitro-5-(2',4'-dicyanophenoxy)benzoate;

methyl 2-nitro-5-[2'-dimethylamino-4'-(α,α,α-trifluoromethyl)phenoxy]benzoate;

ethyl 2-nitro-5-[2'-amino-4'-(α,α,α-trifluoromethyl)-phenoxy]benzoate;

methyl 2-nitro-5-[2'-methyl-4'-methylthiophenoxy]benzoate;

N,N-dimethyl 2-nitro-5[2',6'-dimethyl-4'-methylthiophenoxy]benzamide;

methyl 2-nitro-5-[2'-methyl-b 4'-methylsulfonylphenoxy]benzoate;

ethyl 2-nitro-5-[2'-chloro-4'-methylsulfinylphenoxy]-benzoate;

methyl 2-nitro-5-[4'-(N-trifluoromethylsulfonamido)-phenoxy]benzoate;

methyl 2-nitro-5-(4'-cyanophenoxy)benzoate;

ethyl 2-nitro-5-(4'-carboethoxyphenoxy)benzoate;

methyl 2-nitro-5-(4'-hydroxyphenoxy)benzoate;

2-nitro-5-[2'-t-butylphenoxy]benzoic acid;

2-nitro-5-[2'-carboxyphenoxy]benzoic acid;

methyl 2-nitro-5-(4'-aminophenoxy)benzoate;

methyl 2-nitro-5-(4'-diethylaminophenoxy)benzoate;

methyl 2-nitro-5-(2'-methylaminophenoxy)benzoate;

methyl 2-nitro-5-(4'-mercaptophenoxy)benzoate;

ethyl 2-nitro-5-(4'-methylthiophenoxy)benzoate;

methyl 2-nitro-5-(2'-sulfonamidophenoxy)benzoate;

ethyl 2-nitro-5-(4'-methylsulfinylphenoxy)benzoate;

methyl 2-nitro-5-(4'-methylsulfonylphenoy)benzoate; and 2-nitro-5-(2',4'-dichlorophenoxy)thiobenzoic acid.

The following example illustrates the preparation of a typical compound of this invention and demonstrates a method for product recovery.

EXAMPLE 1

Methyl 2-nitro-5-(2',4',6'-trichlorophenoxy)benzoate

A stirred solution of methyl 5-chloro-2-nitro-benzoate (17.0 g., 0.079 mole) and the potassium salt of 2,4,6-trichlorophenol (18.6 g, 0.079 mole) in dimethyl sulfoxide (100 ml.) was heated at 90° C. for 17 hours. The cooled reaction mixture was diluted with water (500 ml.) and then extracted with ether (3×100 ml.). The combined ether fractions were washed with 10% sodium hydroxide solution (2×30 ml.) and then with a saturated aqueous sodium chloride solution. The ether solution was dried ($Na_2SO_4$) and the solvent evaporated to give a dark oil. Two crystallizations (petroleum ether) gave 1.91 g. of a pale yellow solid, m.p. 101°–103° C.

Example 1

IR(nujol): c=o 1723, c—o 1240, and 1260 $cm^{-1}$

NMR ($CDCl_3$): methyl 3.91 ppm (3H), quartet 6.96 ppm (1H, J=2.5 and 8 c.p.s.), doublet 7.05 ppm (1H, J=2.5 c.p.s.), broad singlet 7.05 ppm (2H), and doublet 801 ppm. (1H, J=8 c.p.s.)

EXAMPLES 2 THROUGH 24

Using procedures similar to that described in Example 1, twenty-three other compounds within the scope of this invention were prepared. These compounds are (2) 2-nitro-5-(2',4',6'-trichlorophenoxy)benzoid acid, m.p. 184°–189° C.

(3) sodium 2-nitro-5-(2',4',6'-trichlorophenoxy)benzoate m.p. >300° C.

(4) methyl 2-nitro-5-(2',4',5'-trichlorophenoxy)benzoate m.p. 100°–103° C.

(5) methyl 2-nitro-5-(2',4'-dichlorophenoxy)benzoate, m.p. 84°–86° C.

(6) ethyl 2-nitro-5-(2',4',6'-trichlorophenoxy)benzoate, m.p. 60°–64° C.

(7) methyl 2-nitro-5-(2',4'-dibromophenoxy)benzoate, m.p. 98°–100° C.

(8) methyl 2-nitro-5-(4'-chloro-2'-methylphenoxy)benzoate, m.p. 70°–72° C.

(9) methyl 2-nitro-5-(2',4'-dimethylphenoxy)benzoate, oil.

(10) 2-nitro-5-(2',4'-dichlorophenoxy)benzamide, m.p. 130°–133° C.

(11) isopropyl 2-nitro-5-(2',4',6'-trichlorophenoxy)benzoate, m.p. 71°–74° C.

(12) ethyl 2-nitro-5-(2',4'-dichlorophenoxy)benzoate, m.p. 83°–85° C.

(13) isopropyl 2-nitro-5-(2',4'-dichlorophenoxy)benzoate, m.p. 59°–62° C.

(14) methyl 2-nitro-5-(2',4',6'-trichlorophenoxy)thiobenzoate, m.p. 96°–100° C.

(15) methyl 2-nitro-5-(2',4'-dichloro-6'-methylphenoxy)benzoate, m.p. 85°–89° C.

(16) methyl 2-nitro-5-(2'-chloro-4'-fluorophenoxy)benzoate, m.p. 67°–70° C.

(17) isopropyl 2-nitro-5-(2'-chloro-4'-fluorophenoxy)benzoate, m.p. 48°–51° C.

(18) N-methyl 2-nitro-5-(2',4'-dichlorophenoxy)benzamide, m.p. 137° C.

(19) ethyl 2-nitro-5-(4'-nitrophenoxy)benzoate, m.p. 75°–82° C.

(20) methyl 2-nitro-5-(3'-methyl-4'-nitrophenoxy)benzoate, m.p. 75°–82° C.

(21) isopropyl 2-nitro-5-[2'-nitro-4'-(α,α,α-trifluoromethyl) phenoxy]benzoate, oil.

(22) ethyl 2-nitro-5-[2'-nitro-4'-(α,α,α-trifluoromethylphenoxy]benzoate, oil.

(23) methyl 2-nitro-5-[2'-chloro-4'-nitrophenoxy]benzoate, m.p. 97°–102° C.

(24) 2-nitro-5-(2'-chloro-4'-nitrophenoxy)benzoic acid, m.p. 185° C.

EXAMPLE 25

2-Nitro-5-[2'-nitro-4'-(α,α,α-trifluoromethyl) phenoxy]benzoic acid

A stirred solution of 4-chloro-3-nitrobenzotrifluoride (22.55, 0.1 mole) and the potassium salt of 3-methyl-4-nitrophenol (19.12 g, 0.1 mole) in dimethyl acetamide (75 ml) was heated at 150° for 4 hours. The cooled reaction solution was diluted with water (300 ml) to precipitate a brown solid which was filtered and dried to give 28.9 g (85%) of 4-nitro-3-tolyl-2'-nitro-α,α,α-trifluoro-4'-tolyl ether, which had an m.p. of 82°–85° C. To a stirred solution of the above diphenyl ether product (25.0 g, 0.073 mole) and sodium dichromate (35.8 g, 0.12 mole) in glacial acetic acid (200 ml) was added concentrated sulfuric acid (60 ml, 1.15 moles) over about 30 minutes. The temperature was maintained below 70° C. during the addition and then raised to 110° C. for 15 hours. The reaction solution was cooled to 60° C. and extracted with hot chloroform. The extract was evaporated to dryness to give an oily solid, which was leached free of starting material with an ether-ligroin mixture. The resulting off-white solid acid weighed 13.6 g (51%), m.p. 185°–187°.

EXAMPLE 26

2-Nitro-5-[2'-nitro-4'-(α,α,α-trifluoromethyl) phenoxy]benzoic acid methyl ester A stirred solution of the acid from Example 6 (3.5 g, 0.0094 mole) in a 25 wt. %/vol. solution of borontrifluoride in methanol (50 ml) was refluxed for 10 hours. The cooled solution was poured onto water (250 ml) and the resulting oil separated and dried to give 3.4 g (93.5%) of the desired product.

EXAMPLE 27

Methyl 2-nitro-5-(2',4'-dichlorophenoxy) thiobenzoate

Into a solution of 2-nitro-5-(2',4'-dichlorophenoxy) benzoyl chloride (4.16 g., 0.012 mole), prepared from the corresponding acid, in 40 ml. benzene was bubbled methanethiol gas for 0.5 hour at room temperature. The gas bubbling was stopped and the reaction mixture was refluxed for 15 minutes and then cooled. The mixture was diluted with diethyl ether, washed twice with 10% aqueous NaOH, once with NaCl solution, dried, and evaporated to dryness to give 4.3 g. of an oil. Infrared analysis showed a large amount of initial benzoyl chloride was unreacted. The oil was dissolved in 100 ml. benzene and 1.5 g. triethylamine was added. The reaction mixture was heated to 65°–70° C. and methanethiol was bubbled in. There was an immediate precipitate. After 1.5 hours, the reaction mixture was cooled, filtered, and evaporated to dryness to give 4.6 g. of the desired product.

EXAMPLE 28

Ethyl 2-nitro-5-(2',4'-dichlorophenoxy) thiobenzoate

A mixture of 2-nitro-5-(2',4'-dichlorophenoxy) benzoyl chloride (4.16 g., 0.012 mole) and ethanethiol (2.24 g., 0.036 mole) in 40 ml. benzene was heated at reflux for 2 hours and 50 minutes and then cooled. The mixture was diluted with diethyl ether, washed twice with 10% aqueous NaOH, once with NaCl solution, dried, and evaporated to dryness to give 4.2 g. of an oil. Infrared analysis showed a large amount of initial benzoyl chloride and some desired product. The oil was dissolved in 100 ml. benzene and 3.0 g. ethanethiol and about 1.5 g. triethylamine were added. A precipitate formed immediately. The reaction mixture was refluxed for 1.5 hours, cooled, filtered and evaporated to dryness to give 4.65 g. of the desired product.

COMPARATIVE EXAMPLE

A series of compounds were prepared which are position isomers of the compounds of Example 1 through 4. Each compound is designated by the number of the corresponding isomeric compound of Examples 1 through 4, followed by "a" or "b". These compounds are:

(1a) methyl 5-nitro-2-(2',4',6'-trichlorophenoxy) benzoate, m.p. 128°–133° C.

(2a) 5-nitro-2-(2',4',6'-trichlorophenoxy)benzoic acid, m.p. 175°–177° C.

(2b) 4-nitro-2-(2',4',5'-trichlorophenoxy)benzoic acid, m.p. 190°–193° C.

(3a) sodium 5-nitro-2-(2', 4', 6'-trichlorophenoxy)benzoate, m.p. >300° C.

(4a) methyl 5-nitro-2-(2', 4', 5'-trichlorophenoxy) benzoate, m.p. 104°–106° C.

(4b) methyl 4-nitro-2-(2', 4', 5'-trichlorophenoxy)benzoate, m.p. 127°–131° C.

As is apparent from the date in the Table set forth hereinafter, the compounds embodied herein in which the nitro group is in the 2-position and the substituted phenoxy group is in the 5-position exhibit markedly higher effectiveness as herebicides than do the comparable compounds in which the nitro group and the substituted phenoxy group are in different positions.

The compounds of this invention can be applied in various ways to achieve herbicidal action. They can be applied, per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carries, include water; organic solvents, such as alcohols, ketones, amides and esters; mineral oils, such as kerosene, light oils, and medium oils and vegetable oils, such as cottonseed oil.

In practice, herbicidal application is measured in terms of pounds of herbicide applied per acre. The compounds of this invention are effective herbicides when applied in herbicidal amounts, i.e., at rates between about 0.2 pounds and about 10 pounds per acre.

HERBICIDAL EFFECTIVENESS

Method of Propagating Test Species

| | |
|---|---|
| Crabgrass | Digitaria sanguinalis |
| Yellow Foxtail grass | Setaria glauca |
| Johnson grass | Sorgum Halepense |
| Barnyard grass | Echinochloe crus-galli |
| Amaranth pigweed | Amaranthus retroflexus |
| Turnip | Brassica sp. |
| Cotton | Gossypium hirsutum var. DPL smooth leaf |
| Corn | Zea Mays var. Golden Bantam |
| Bean | Phaseolus vulgaris var. Black Valentine |

All crop and weed species are planted individually in 3" plastic pots containing potting soil. Four seeds of each of corn, cotton, and snapbeans are seeded to a depth equal to the diameter of the seed. All other species are surface seeded and sprinkled with screened soil in an amount sufficient to cover the seeds. Immediately after planting, all pots are watered by sub-irrigation in greenhouse trays. Pots for the pre-emergence phase are seeded one day before treatment.

Planting dates for the post-emergence phase are varied so that al the seedlings will reach the desired state of development simultaneously. The proper state of seedling development for treatment in the post-emergence phase is as follows:

GRASSES: 2 inches in height
PIGWEED & TURNIPS: 1 or 2 true leaves visible above cotyledons.
COTTON: first true leaf 1 inch in length; expanded cotyledons.
CORN: 3 inches–4 inches in height
BEANS: primary leaves expanded, growing point at primary leaf node.

Method of Treatment

Spray applications are made in a hood containing movable belt and fixed spray nozzle. For passage through the spray hood, one pot of each species (pre-emergence phase) is placed on the forward half of a wooden flat and one pot of established plants (post-emergence phase) is placed on the rear half of the flat. Treatments are moved to the greenhouse after spraying. Watering during the observatin period is applied only by sub-irrigation.

Compounds are screened initially at a rate of application equivalent to four or eight pounds per acre. Two weeks after treatment the pre- and post-emergence percent effectiveness is visually rated. Subsequent testing is carried out at 2,1 and 0.5 pounds per acre.

Herbicidal testing of the compounds of Examples 1 through 28 and of the comparative compounds provided the results set forth in the Table. The plants are tabulated using the following abbreviations:

| Crabgrass | CG | Pigweed | PW |
| Yellow Foxtail grass | YF | Turnip | TP |
| Johnson grass | JG | Cotton | CT |
| Barnyard grass | BG | Corn | CN |
| Bean | BN | | |

TABLE

PRE/POST-EMERGENCE HERBICIDAL ACTIVITIY* OF CERTAIN SUBSTITUTED PHENOXYBENZOIC ACIDS AND DERIVATIVES THEREOF

| COMPOUND OF EXAMPLE | COMPOUND CONCENTRATION, LBS./ACRE | CG | YF | JG | BG | PW | TP | CT | CN | BN |
|---|---|---|---|---|---|---|---|---|---|---|
| 1 | 4 | 100/100 | 100/100 | 60/50 | 60/70 | 100/100 | 80/100 | 0/100 | 0/40 | 30/100 |
|  | 2 | 100/100 | 80/100 | 30/70 | 20/80 | 100/100 | 0/100 | 90/100 | 30/20 | 70/100 |
|  | 1 | 100/90 | 80/100 | 20/60 | 0/60 | 100/100 | 30/90 | 0/100 | 0/20 | 80/100 |
|  | 0.5 | 40/50 | 60/80 | 30/60 | 0/40 | 100/70 | 0/80 | 40/20 | 0/20 | 30/70 |
| 1a (Comparative) | 4 | 20/20 | 0/20 | 0/20 | 0/20 | 20/0 | 0/30 | 100/0 | 50/0 | 20/80 |
| 2 | 4 | 70/70 | —/— | 70/90 | 60/70 | —/— | 100/100 | 0/100 | 0/70 | 80/70 |
| 2a (Comparative) | 4 | 20/30 | 0/20 | 20/30 | 0/20 | —/20 | 30/90 | 50/20 | 0/0 | 50/70 |
| 2b (Comparative) | 4 | 0/30 | 40/0 | 50/30 | 20/20 | 20/20 | 0/50 | 40/20 | 30/30 | 80/0 |
| 3 | 4 | 50/80 | —/— | 30/60 | 40/60 | —/— | 95/100 | 50/100 | 0/40 | 50/100 |
| 3a (Comparative) | 4 | 0/20 | 0/20 | 0/20 | 0/20 | 50/50 | 0/60 | 100/0 | 30/0 | 50/40 |
| 4 | 4 | 90/60 | —/— | 80/90 | 50/50 | —/— | 40/70 | 80/70 | 0/50 | 80/80 |
| 4a (Comparative) | 8 | 30/30 | 0/20 | 20/30 | 0/20 | 30/30 | 40/0 | 0/30 | 0/0 | 60/0 |
| 4b (Comparative) | 4 | 20/20 | 0/20 | 0/20 | 0/20 | 0/20 | 0/60 | 30/50 | 0/30 | 0/60 |
| 5 | 4 | 100/95 | —/— | 90/90 | 90/90 | —/— | 80/100 | 50/80 | 0/40 | 50/100 |
| 6 | 4 | 100/80 | —/— | 80/50 | 50/70 | 100/100 | 40/90 | 30/100 | 0/100 | 100/100 |
| 7 | 8 | 80/60 | —/— | 50/40 | 60/50 | 100/100 | 20/100 | 30/90 | 0/50 | 100/100 |
| 8 | 8 | 50/60 | —/— | 20/30 | 0/20 | 100/100 | 0/40 | 0/30 | 100/100 |  |
| 9 | 8 | 30/30 | —/— | 0/40 | 20/20 | 90/90 | 20/50 | 0/70 | 0/40 | 100/90 |
| 10 | 4 | 80/70 | —/— | 40/40 | 40/30 | 100/100 | 20/70 | 100/40 | 0/20 | 100/100 |
| 11 | 4 | 60/70 | —/— | 30/60 | 20/50 | 90/100 | 0/50 | 30/70 | 0/30 | 80/60 |
| 12 | 8 | 90/90 | —/— | 90/90 | 60/90 | 100/100 | 0/100 | 0/100 | 0/70 | 0/100 |
|  | 4 | 100/90 | —/— | 90/100 | 60/60 | 100/100 | 0/100 | 30/90 | 0/70 | 30/100 |
|  | 2 | 100/100 | 100/— | 40/60 | 80/70 | —/100 | 30/100 | 80/70 | 0/70 | 100/100 |
|  | 1 | 100/100 | —/— | 40/90 | 50/80 | —/— | 30/100 | 20/80 | 0/20 | 50/80 |
| 13 | 8 | 70/90 | —/— | 30/90 | 20/80 | 90/100 | 0/30 | 30/70 | 0/20 | 100/100 |
| 14 | 4 | 70/80 | —/— | 20/90 | 0/40 | 100/100 | 70/100 | 90/90 | 20/20 | 0/80 |
| 15 | 8 | 100/100 | 100/— | 50/70 | 50/— | —/100 | 70/90 | 0/90 | 0/30 | 50/100 |
|  | 4 | 90/90 | 0/— | 40/60 | 0/60 | —/— | 60/90 | 100/60 | 0/40 | 0/100 |
|  | 2 | 90/70 | —/— | 30/40 | 20/70 | —/— | 70/60 | 0/60 | 0/50 | 0/100 |
| 16 | 8 | 100/90 | 100/100 | 80/100 | 100/90 | 100/100 | 100/100 | 40/100 | 80/40 | 80/100 |
|  | 4 | 100/100 | 100/100 | 100/100 | 80/80 | 100/100 | 70/100 | 40/90 | 20/80 | 80/100 |
|  | 2 | 100/100 | 100/100 | 90/100 | 80/90 | 100/100 | 80/100 | 30/90 | 0/80 | 0/90 |
|  | 0.8 | 90/60 | 100/80 | 70/50 | 40/50 | 100/100 | 40/100 | 80/60 | 30/20 | 50/100 |
| 17 | 8 | 100/40 | 90/40 | 70/40 | 50/30 | 100/100 | 0/60 | 0/80 | 0/30 | 0/90 |
|  | 4 | 100/90 | 100/100 | 80/90 | 50/70 | 100/100 | 0/40 | 0/50 | 0/30 | 0/90 |
|  | 2 | 100/90 | 100/90 | 30/90 | 30/90 | 100/100 | 20/30 | 0/50 | 0/30 | 0/90 |
|  | 1 | 60/50 | 100/80 | 90/60 | 20/30 | 100/100 | 0/40 | 90/30 | 30/0 | 80/80 |
| 18 | 8 | 90/80 | —/— | 60/80 | 70/40 | —/— | 90/100 | 30/80 | 0/80 | 0/100 |
| 19 | 10 | 40/30 | —/— | 90/— | —/— | —/— | 0/90 | —/60 | —/— | —/60 |
| 20 | 10 | 50/20 | —/— | 90/— | —/— | —/— | 20/20 | —/30 | —/— | —/40 |
| 21 | 3 | 100/— | 100/— | 100/— | 30/— | —/— | 50/— | 30/— | 0/— | 0/— |
| 22 | 1 | 90/— | 100/— | 100/— | 30/— | —/— | 30/— | 50/— | 60/— | 0/— |
| 23 | 10 | 80/— | 100/— | 100/— | 30/— | —/— | 80/— | —/— | —/— | —/— |
| 24 | 10 | 100/— | —/— | 30/— | —/— | —/— | 100/— | —/— | —/— | —/— |
| 25 | 8 | 80/70 | 90/100 | 50/40 | 30/60 | 100/100 | 100/100 | 30/50 | 0/30 | 30/90 |
| 26 | 8 | 100/80 | 100/90 | 40/20 | 90/60 | 100/100 | 90/90 | 0/50 | 0/20 | 70/90 |
|  | 4 | 100/90 | 100/100 | 70/90 | 80/50 | 100/100 | 100/100 | 0/50 | 0/20 | 0/90 |

TABLE-continued
PRE/POST-EMERGENCE HERBICIDAL ACTIVITIY* OF CERTAIN SUBSTITUTED PHENOXYBENZOIC ACIDS AND DERIVATIVES THEREOF

| COMPOUND OF EXAMPLE | COMPOUND CONCENTRATION, LBS./ACRE | CG | YF | JG | BG | PW | TP | CT | CN | BN |
|---|---|---|---|---|---|---|---|---|---|---|
|  | 2 | 90/70 | 100/100 | 60/60 | 40/70 | 100/100 | 90/90 | 0/50 | 0/30 | 0/90 |
| 27 | 8 | 20/30 | 80/— | —/— | —/— | —/— | 100/100 | —/100 | —/— | —/100 |
| 28 | 8 | 0/30 | —/— | —/— | —/— | —/— | 100/100 | —/100 | —/— | —/100 |

*Herbicidal activity is measured in percent effectiveness

Although the present invention has been described with preferred embodiments, it is to be understood that modifications and variations may be resorted to without departing from the spirit and scope of this invention, as those skilled in the art will readily understand. Such modifications and variations are considered to be within the purview and scope of the appended claims.

What is claimed is:

1. An herbicidal composition comprising as an effective herbicide, a herbicidally effective quantity of 2-nitro-5-(substituted-phenoxy) benzoic acid, salts thereof selected from the group consisting of lithium salts, sodium salts, potassium salts, alkylammonium salts of 1 to 4 carbon atoms and alkanolammonium salts of 1 to 4 carbon atoms, alkyl esters thereof of 1 to 5 carbon atoms and the phenyl ester thereof, wherein said phenoxy is substituted only by a combination of two members selected from the group consisting of halogen, trifluoromethyl, COOH,

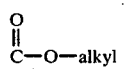

alkyl of 1 to 4 carbon atoms), hydroxy, alkoxy of 1 to 4 carbon atoms,

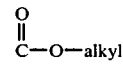

SH, $SR_1$, $SOR_1$, $SO_2R_1$, $SO_2NH_2$ wherein $R_1$ and $R_2$ are selected from the group consisting of alkyl of 1 to 4 carbon atoms, and an agronomically acceptable carrier selected from the group consisting of solid carriers, water and organic solvents.

2. A composition according to claim 1 wherein said carrier is a solid carrier selected from the group consisting of talc, bentonite, diatomaceous earth, pyropyllite, fullers earth, gypsum, cotton seed flour, nut shell flour, natural clays and synthetic clays, said clays having a pH not exceeding about 9.5.

3. A composition according to claim 1 wherein said carrier is water.

4. A composition according to claim 1 wherein said carrier is an organic solvent.

5. A composition according to claim 1 wherein one member of said combination is halogen.

6. A composition according to claim 5 wherein one member of said combination is trifluoromethyl.

7. A composition according to claim 1 wherein one member of said combination is trifluoromethyl.

8. A method for controlling plant growth which comprises applying a composition consisting essentially of: an herbicidal amount of a compound having the formula:

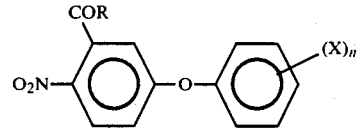

wherein $(X)_n$ is a combination of the members selected from the group consisting of halogen, trifluoromethyl, COOH,

(alkyl having 1 to 4 carbon atoms), hydroxy, alkoxy having 1 to 4 carbon atoms, $$N{\begin{matrix}R_1\\R_2\end{matrix}},$$

SH, $SR_1$, $SOR_1$, $SO_2R_1$, $SO_2NH_2$; $R_1$ and $R_2$ are selected from the group consisting of alkyl having 1 to 4 carbon atoms, R is selected from the group consisting of hydroxy, alkoxy having 1 to 5 carbon atoms, and OM wherein M is an alkali metal of lithium, sodium or potassium, alkylammonium having 1 to 4 carbon atoms or alkanolammonium having 1 to 4 carbon atoms and n is the integer 2; and an agronomically acceptable carrier selected from the group consisting of solid carriers, water and organic carriers.

9. A method according to claim 8 wherein an X is trifluoromethyl.

10. A method according to claim 8 which comprises applying said composition to the surface of a growth medium, prior to the emergence of the plants from the growth medium.

11. A method according to claim 8 which comprises applying said composition to plant seedlings after their emergence.

12. A method according to claim 8 which comprises spraying plants with an herbicidally effective amount of said composition.

13. A method according to claim 8 wherein an X is halogen.

14. A method according to claim 13 wherein an X is trifluoromethyl.

15. A method according to claim 8 which comprises applying to plants said compound at a rate of about 0.2 to about 10 pounds per acre.

* * * * *